US00PP34404P2

(12) United States Plant Patent
Bradford et al.

(10) Patent No.: US PP34,404 P2
(45) Date of Patent: Jul. 5, 2022

(54) NECTARINE TREE NAMED 'CANDYSWEET XIV'

(50) Latin Name: *Prunus persica*
Varietal Denomination: 'Candysweet XIV'

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,924

(22) Filed: Dec. 17, 2021

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
CPC ..... A01H 6/7454; A01H 5/08
See application file for complete search history.

(56) References Cited

U.S. PATENT DOCUMENTS

PP21,927 P2 5/2011 Bradford

*Primary Examiner* — Keith O. Robinson

(57) ABSTRACT

The present invention relates to a new and distinct variety of nectarine tree, *Prunus persica*, broadly characterized by a medium size, vigorous, hardy, self-fertile, productive and regular bearing tree. The variety has a large showy blossom and blooms during the mid season, with a chilling requirement of about 550 hours. The fruit matures under the ecological conditions described in late July, with first picking on Jul. 21, 2021. The fruit is uniform, large in size, sub-acidic and very sweet in flavor, globose in shape, clingstone in type, firm in texture, yellow in flesh color, red to orange with considerable freckling in skin color, and has a bitter tasting kernel.

1 Drawing Sheet

Botanical classification: *Prunus persica.*
Variety denomination: 'CANDYSWEET XIV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Candysweet XIV'.

During the fruit season of 2011 we gathered fruit from many of our newest and best selections to grow their open pollinated seeds. One group of the late maturing nectarines and peaches was gathered, and the seeds were removed, cracked, stratified, germinated as a group with the label "Late P&N", and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2016 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to 'Giant Bright' (U.S. Plant Pat. No. 21,927) nectarine by having a medium size tree, by having reniform leaf glands, by being self-fertile, and by producing nectarines that are mostly red in skin color, that are yellow in flesh color, that are large in size, that are clingstone in type, that are firm in texture, and that mature in late July, but is distinguished therefrom by blooming about ten days earlier, by requiring less chilling hours, by having a large instead of small blossom and by producing nectarines that have a stronger amount of skin freckling, that have more red bleeding in the flesh, that are sub-acidic instead of acidic in flavor, that are much sweeter, that ripen about four days later, and that have a bitter instead of sweet kernel.

SUMMARY OF VARIETY

In summary, the present nectarine variety is characterized by a medium size, vigorous, hardy, self-fertile, productive and regular bearing tree. The variety has a large showy blossom and blooms during the mid season, with a chilling requirement of about 550 hours. The fruit matures under the ecological conditions described in late July, with first picking on Jul. 21, 2021. The fruit is uniform, large in size, sub-acidic and very sweet in flavor, globose in shape, clingstone in type, firm in texture, yellow in flesh color, red to orange with considerable freckling in skin color, and has a bitter tasting kernel.

DRAWING

The accompanying photograph consists of four whole fruits positioned to display the characteristics of the skin color and form, one divided fruit to reveal the flesh and stone, a tip shoot of new leaf growth, typical leaves, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 27, 2021, on the original tree during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: Unknown.
Pollen parent: Unknown.

TREE

Size: Medium, reaching and maintaining a height of 10' [3.05 m.] and a spread of 9' [2.74 m.] after ten growing seasons utilizing typical dormant pruning.
Vigor: Vigorous, responding about average to irrigation and fertilization. The variety grows about 2' [0.61 m.] of surplus top-growth during the spring and summer. The plant should be grown on a standard commercial rootstock for production purposes.
Growth: Upright and dense.
Form: Pruned to a vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Chilling requirement: About 550 hours.
Leaf bud burst: Medium, during the middle of flowering.
Trunk:
- *Size.*—Medium, reaching a maximum diameter of 5¼" [133 mm.] after the tenth growing season.
- *Texture.*—Medium to shaggy.
- *Bark color.*—A Grayish yellowish brown [80. gy.yBr] and Grayish brown [61. gy.Br] variegation with Dark Grayish brown [62. d.gy.Br] crevices present.
- *Lenticels.*—Approximate Number Per Square Inch: 8. Color: Strong yellowish brown [74. s.yBr]. Average Size: ⅜" [9.5 mm.] in length. The width is typically one fourth as much as the length. Shape: Elongated.

Branches:
- *Size.*—Medium, diameter of main scaffold is 2¾" [69.9 mm.] measured 12" above the crotch, diameter of limb is 2" [50.8 mm.] measured 12" above the first fork.
- *Texture.*—Smooth to medium on first and second year wood, increasing in roughness with age.
- *Color.*—1st Year Wood Topside: Grayish red [19. gy.R]. 1st Year Wood Underside: Brilliant yellow green [116. brill.YG]. Older Wood: A Deep yellowish brown [75. deep yBr] and Strong yellowish brown [74. s.yBr] variegation with Dark yellowish brown [78. d.yBr] crevices present.
- *Lenticels.*—Number Per Square Inch: About 20 on second year wood. Color: Dark orange yellow [72. d.OY]. Average Size: Small, 1/16" [1.6 mm.] in length. The width is typically one fourth as much as the length. Shape: Elongated.

Leaves:
- *Size.*—Large to medium. Average Length: 5¾" [146.1 mm.]. Average Width: 1⅞" [47.6 mm.].
- *Arrangement.*—Alternate.
- *Thickness.*—Medium.
- *Form.*—Elliptical.
- *Apex.*—Acuminate.
- *Base.*—Acute with an average base angle of seventy-five degrees.
- *Surface.*—Smooth on both sides.
- *Color.*—Dorsal Surface: Moderate olive green [125. m.OlG]. Ventral Surface: Moderate yellow green [120. m.YG].
- *Red midvein.*—Absent.
- *Margin.*—Finely serrate.
- *Venation.*—Pinnately net veined.
- *Petiole.*—Average Length: ½" [12.7 mm.]. Average Thickness: 1/16" [1.6 mm.]. Color: Pale greenish yellow [104. p.gY].
- *Stipules.*—Number: 2 per leaf, up to 6 per growing tip. Average Length: ¼" [6.4 mm.]. Color: Light yellow green [119. l.YG] becoming Grayish red [19. gy.R] with age.
- *Glands.*—Number: 2 to 4 per leaf. Position: Both alternate and opposite, first pair is located at the intersection of petiole and base of blade. Form: Reniform. Size: Medium, about 1/32" [0.8 mm.] in length, about 1/64" [0.4 mm.] in width. Color: Moderate olive green [125. m.OlG].
- *Leaf buds.*—Pointed.

Flower buds:
- *Hardiness.*—Hardy, with respect to central California blooming season.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Pubescent.
- *Tip color.*—Pale purplish pink [252. p.pPk].

Flowers: Perfect, complete, perigynous, usually a single pistil, about thirty stamens, five sepal and petal locations alternately positioned.
- *Type.*—Showy, large.
- *Average flower diameter.*—1¾" [44.5 mm.].
- *Average flower depth.*—½" [12.7 mm.] when fully open.
- *Number of petals.*—Five, extra petal fragments ocassionally observed, double blossoms not observed.
- *Petal arrangement.*—Overlapping.
- *Petal shape.*—Circular to oval.
- *Petal margin.*—Entire, wavy.
- *Average petal diameter.*—¾" [19.1 mm.].
- *Average petal length.*—13/16" [20.6 mm.].

*Petal apex.*—Rounded.
*Petal base.*—Rounded to slightly obtuse.
*Petal color.*—Pale purplish pink [252. p.pPk] toward the apex and Moderate purplish pink [250. m.pPk] toward the base on both sides.
*Anthocyanin coloration intensity.*—Slight.
*Anther color.*—Moderate red [15. m.R] surrounding a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located slightly about even with the nearby anthers.
*Stamen position.*—Typically located about 1/16" [1.6 mm] below the petals.
*Average pistil length.*—3/4" [19.1 mm.].
*Average stamen length.*—9/16" [14.3 mm.].
*Ovary.*—Non-pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—3/8" [9.5 mm.].
*Sepal width.*—5/16" [7.9 mm.].
*Sepal apex.*—Rounded to elliptical to match the sepal length and width.
*Sepal margin.*—Fairly smooth.
*Sepal outer surface.*—Pubescent.
*Fragrance.*—Moderate in degree with a slight hint of rose.
*Blooming period.*—Medium, blooms about the same time as 'Majestic Pearl' (U.S. Plant Pat. No. 18,778) nectarine.
*Onset of bloom.*—One percent on Feb. 20, 2021.
*Date of full bloom.*—Mar. 4, 2021.
*Duration of bloom.*—One to two weeks, dependent on ambient temperature.
*Bloom density.*—Medium to heavy.
*Number per cluster.*—1 to 3 with single flowers most common.

FRUIT

Maturity when described: Firm ripe, Jul. 27, 2021.
Date of first picking: Jul. 21, 2021.
Date of last picking: Aug. 6, 2021.
Size: Uniform, large.
*Average diameter axially.*—3" [76.2 mm.].
*Average diameter across suture plane.*—3 1/8" [79.4 mm.].
*Average diameter across cheek plane.*—3 1/16" [77.8 mm.].
*Typical weight.*—9.8 ounces [277 grams].
Form: Uniform, globose, mostly symmetrical.
*Longitudinal section form.*—Round to slightly oval.
*Axial view.*—Round.
Suture: Extends from the stem cavity, continues along the side, and ends with a slight depression just beyond pistil point.
*Near the base.*—A shallow groove.
*Along the side.*—A shallow trough.
*Near the apex.*—A moderate groove.
Ventral surface: Rounded, lipped throughout on both sides.
Lips: Mostly equal.
Cavity: Flaring with Vivid orange yellow [66. v.OY] stem markings present.
*Depth.*—1/2" [12.7 mm.].
*Breadth.*—1 3/8" [34.9 mm.].
Base: Somewhat truncate.
Apex: Rounded, cordate if viewed parallel to the suture.
Pistil point: Oblique, depressed within the suture, negligible in length.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to the flesh.
*Astringency.*—Non-astringent.
*Tendency to crack.*—None observed.
*Color.*—Dark red [16. d.R] over a Strong orange yellow [68. s.OY] background with considerable Light yellowish brown [76. l.yBr] freckling on the sides and toward the apex. The primary color covers about seventy percent of the total skin area, and the background color covers about thirty percent.
Flesh:
*Color.*—Brilliant orange yellow [67. brill.OY] with some Vivid red [11. v.R] streaking toward the stone.
*Surface of pit cavity.*—Covered with Vivid red [11. v.R] broken fibers when twisted away from the stone.
*Amygdalin.*—Scarce.
*Juice.*—Moderate.
*Texture.*—Firm, crisp.
*Fibers.*—Few, fine.
*Ripens.*—Fairly even, slightly earlier on the shoulders.
*Flavor.*—Sub-acidic, very sweet, typically 21 brix.
*Aroma.*—Moderate.
*Eating quality.*—Excellent.

STONE

Type: Clingstone.
Size: Medium.
Form: Oval.
Hilum: Narrow, oval.
Base: Rounded.
Apex: Rounded to obtuse.
Sides: Slightly unequal.
Tip: A blunt point, negligible in length.
Surface: Irregularly furrowed toward the apex, pitted toward the base.
Ridges: Jagged.
External color: Deep reddish brown [41. deep rBr] when first removed.
Pit wall color when cracked: Grayish reddish brown [46. gy.rBr].
Cavity surface color: Strong brown [55. s.Br].
Average pit wall thickness: 1/4" [6.4 mm.].
Average length: 1 3/16" [30.2 mm.].
Average width: 1 1/16" [27.0 mm.].
Average breadth: 7/8" [22.2 mm.].
Tendency to split: None observed.
Kernel:
*Form.*—Oval.
*Skin color.*—Brilliant yellow [83. brill.Y].
*Pellicle color.*—Dark yellowish brown [78. d.yBr].
*Vein color.*—Light yellowish brown [76. l.yBr].

*Taste.*—Bitter.
*Viable.*—Yes.
*Average length.*—11/16" [17.5 mm.].
*Average width.*—½" [12.7 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree named 'Candysweet XIV', substantially as illustrated and described, that is most similar to 'Giant Bright' (U.S. Plant Pat. No. 21,927) nectarine by having a medium size tree, by having reniform leaf glands, by being self-fertile, and by producing nectarines that are mostly red in skin color, that are yellow in flesh color, that are large in size, that are clingstone in type, that are firm in texture, and that mature in late July, but is distinguished therefrom by blooming about ten days earlier, by requiring less chilling hours, by having a large instead of small blossom and by producing nectarines that have a stronger amount of skin freckling, that have more red bleeding in the flesh, that are sub-acidic instead of acidic in flavor, that are much sweeter, that ripen about four days later, and that have a bitter instead of sweet kernel.

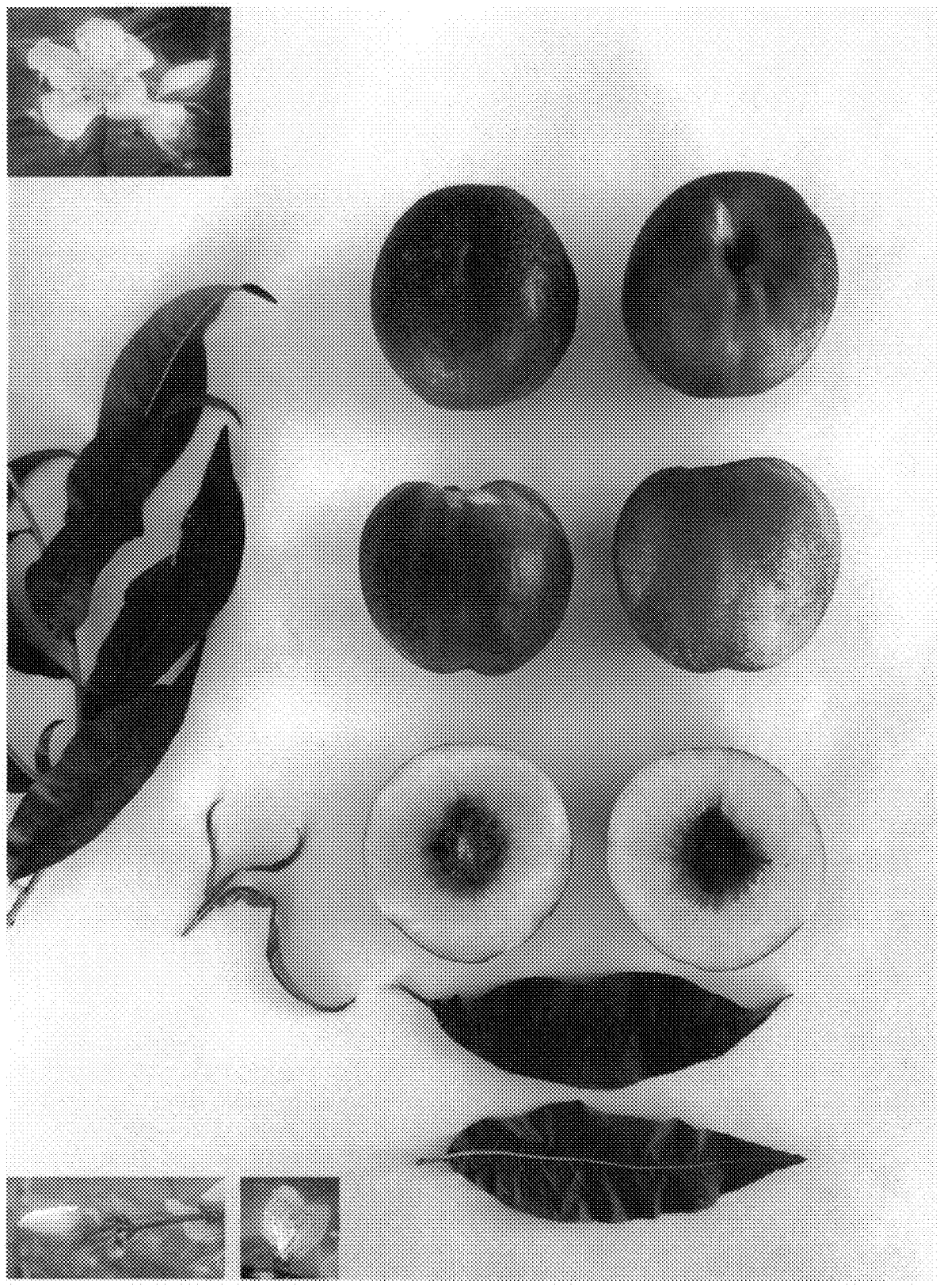

* * * * *